United States Patent
Overmyer et al.

(10) Patent No.: US 10,376,276 B2
(45) Date of Patent: Aug. 13, 2019

(54) CALIBRATION OF A ROBOTIC SURGICAL TOOL

(71) Applicant: Ethicon LLC, Guaynabo, PR (US)

(72) Inventors: Mark D. Overmyer, Cincinnati, OH (US); Jeffrey S. Swayze, West Chester, OH (US); Andrew Beckman, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 155 days.

(21) Appl. No.: 15/422,963

(22) Filed: Feb. 2, 2017

(65) Prior Publication Data
US 2018/0214167 A1    Aug. 2, 2018

(51) Int. Cl.
| A61B 17/29 | (2006.01) |
| A61B 34/30 | (2016.01) |
| A61B 17/00 | (2006.01) |
| A61B 18/14 | (2006.01) |
| A61B 18/00 | (2006.01) |

(Continued)

(52) U.S. Cl.
CPC .............. *A61B 17/29* (2013.01); *A61B 34/30* (2016.02); *A61B 18/14* (2013.01); *A61B 18/1402* (2013.01); *A61B 2017/00725* (2013.01); *A61B 2017/2901* (2013.01); *A61B 2018/00202* (2013.01); *A61B 2018/00988* (2013.01);

(Continued)

(58) Field of Classification Search
CPC ......... A61B 17/29; A61B 34/30; A61B 18/14; A61B 18/1402; A61B 2017/2901; A61B 2017/00725; A61B 2034/302; A61B 2034/2059; A61B 2090/067; A61B 2018/00202; A61B 2018/0098
See application file for complete search history.

(56) References Cited

U.S. PATENT DOCUMENTS

| 8,114,345 B2 | 2/2012 | Dlugos, Jr. et al. |
| 8,894,654 B2 * | 11/2014 | Anderson ............... B23B 49/02 |
| | | 606/80 |

(Continued)

FOREIGN PATENT DOCUMENTS

| EP | 2923669 A1 | 9/2015 |
| WO | WO-2016026511 A1 | 2/2016 |

OTHER PUBLICATIONS

Written Opinion for International App. No. PCT/IB2018050566 dated Apr. 10, 2018.

(Continued)

*Primary Examiner* — Rachid Bendidi

(74) *Attorney, Agent, or Firm* — Mintz Levin Cohn Ferris Glovsky and Popeo, P.C.

(57) ABSTRACT

Systems and methods for calibration of a shaft of a surgical tool are provided. The tool includes an elongate shaft configured to be coupled to an electromechanical arm of a robotic surgical system and having an end effector coupled to a distal end thereof, the shaft being rotatable about its longitudinal axis. The tool also includes at least one target associated with the shaft and configured to be non-independently movable with respect to the shaft, wherein a position of the target is detected using at least one sensor disposed such that the shaft is able to move independently of the sensor. The detected position is used to determine a rotational angle of the shaft. This can involve accessing a memory on the tool or the system storing values related to a target position in association with corresponding values of a shaft rotation angle.

19 Claims, 14 Drawing Sheets

(51) Int. Cl.
*A61B 90/00* (2016.01)
*A61B 34/20* (2016.01)
(52) U.S. Cl.
CPC . *A61B 2034/2059* (2016.02); *A61B 2034/302* (2016.02); *A61B 2090/067* (2016.02)

(56) References Cited

U.S. PATENT DOCUMENTS

| | | | |
|---|---|---|---|
| 9,968,280 B2 * | 5/2018 | Whitcomb | A61B 5/055 |
| 2011/0245833 A1 | 10/2011 | Anderson | |
| 2014/0039298 A1 | 2/2014 | Whitcomb et al. | |
| 2015/0164593 A1 | 6/2015 | Lohmeier et al. | |
| 2015/0265807 A1 * | 9/2015 | Park | A61M 25/0133 600/424 |
| 2017/0224424 A1 * | 8/2017 | Nilsagard | A61B 34/20 |

* cited by examiner

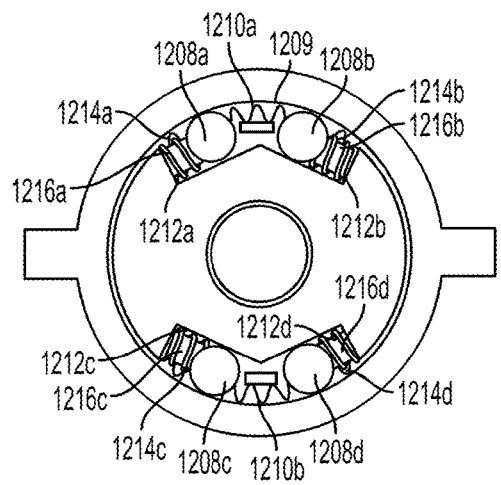
FIG. 13C
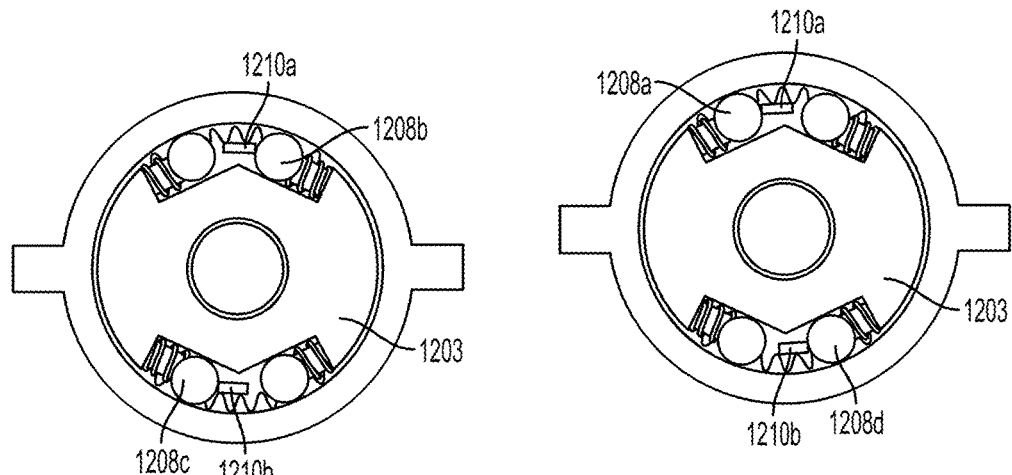
FIG. 14A
FIG. 14B

CALIBRATION OF A ROBOTIC SURGICAL TOOL

FIELD

Methods and devices are provided for robotic surgery, and in particular for calibration of rotating and articulating robotic surgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, systems and methods for calibrating a robotic surgical tool are provided. In particular, systems and methods capable of detecting a rotational angle of an elongate shaft of a surgical tool are provided.

In one aspect, a surgical tool is provided that in some embodiments includes an elongate shaft configured to be coupled to an electromechanical arm of a robotic surgical system and having an end effector coupled to a distal end thereof, the shaft being rotatable about a longitudinal axis of the shaft and at least one target associated with the elongate shaft and configured to be non-independently movable with respect to the shaft, wherein a position of the target is detected using at least one sensor disposed such that the shaft is able to move independently of the sensor, and wherein the detected position is used to determine a rotational angle of the shaft.

The surgical tool can vary in many different ways. For example, the sensor can be coupled to the electromechanical arm of the robotic surgical system and is at a position so as to be remote from the shaft.

The at least one target can also vary in different ways. For example the at least one target can be coupled to the shaft. As another example, the at least one target can be in the form of a portion of the shaft having properties distinct from a remainder of the shaft. The at least one target can be associated with the shaft such that a position of the target, when detected, is used to determine a zero rotational angle position of the shaft.

In at least one embodiment, the target is or includes at least one substantially circular magnetic feature disposed in the shaft coaxially therewith, and the at least one sensor comprises first and second sensors. In another embodiment, the at least one target is or includes at least one portion of the shaft that is magnetized and disposed at least partially along a circumference of the shaft, and the at least one sensor comprises first and second sensors.

In at least one embodiment, the at least one target is or includes at least one portion of the shaft that is disposed at least partially along a circumference of the shaft, the at least one portion having at least one light absorption property that is different from at least one light absorption property of a remainder of the shaft. The at least one sensor can include a transmitter and a receiver.

In at least one embodiment, the at least one target is or includes an elongate magnetic element having first and second ends and disposed substantially helically around the shaft, and the at least one sensor is disposed adjacent to one of the first and second ends. In at least one another embodiment, the at least one target is or includes at least one magnet disposed at a predetermined position along the shaft and offset from a central longitudinal axis of the shaft. In yet at least one another embodiment, the at least one target is or includes at least one substantially circular conductive feature disposed around a circumference of the shaft, and the at least one sensor comprises an inductive sensor.

In some embodiments, the surgical tool includes a memory configured to store a plurality of first values representing positions of the target feature with respect to the sensor, and a plurality of second values representing rotational angles of the shaft each corresponding to respective one of the first values. The tool can be further configured to receive a user-initiated input requesting rotational movement of the shaft with reference to the stored values. The memory can be further configured to store a plurality of first values representing positions of the target feature with respect to the sensor, and a plurality of second values representing rotational angles of the shaft each corresponding to respective one of the first values. The controller can be further configured to receive a user-initiated input requesting rotational movement of the shaft with reference to the stored values.

In another aspect, a method of operating a surgical tool is provided that in some embodiments include detecting a connection between an elongate shaft and an electromechanical arm of a robotic surgical system, the shaft having an end effector coupled to a distal end thereof and being rotatable about a longitudinal axis thereof, and having at least one target associated therewith that is configured to be movable together with the shaft. The method further includes acquiring at least one value corresponding to a position of the target with respect to a sensor, and determining a rotational angle of the elongate shaft based on the acquired value.

The method can vary in many different ways. For example, in some embodiments, the method can include receiving a user-initiated input requesting rotational movement of the shaft to position the shaft such that the sensor is able to acquire the at least one value indicating the position of the target with respect to the sensor.

In some embodiments, the method can include accessing a storage storing a plurality of first values representing positions of the target feature with respect to the sensor, and a plurality of second values representing rotational angles of the shaft each corresponding to respective one of the first values, comparing the acquired value to the plurality of first values to identify a matching first value, and determining the rotational angle of the shaft based on a second value of the plurality of second values that corresponds to the matching first value. The at least one value can be a voltage value.

In another aspect, a robotic surgical system is provided that in some embodiments includes a surgical tool having an elongate shaft configured to be coupled to an electromechanical arm of the robotic surgical system and having an end effector coupled to a distal end thereof, the shaft being rotatable about a longitudinal axis thereof, and at least one target associated with the shaft and configured to be non-independently movable with respect to the shaft. The robotic surgical system also includes at least one sensor disposed on the electromechanical arm and configured to detect a position of the target, wherein the detected position is used to determine a rotational angle of the shaft. The robotic surgical system also includes a memory configured store a plurality of first values representing positions of the target feature with respect to the sensor, and a plurality of second values representing rotational angles of the shaft each corresponding to respective one of the first values. The robotic surgical system can also include a controller configured to access the memory to determine the rotational angle of the elongate shaft based on a comparison of the detected position of the target with the plurality of first values.

BRIEF DESCRIPTION OF THE DRAWINGS

The present disclosure will be more fully understood from the following detailed description taken in conjunction with the accompanying drawings, in which:

FIG. 13C is a cross-sectional view, from a distal end, of the shaft locking mechanism of FIG. 13B;

FIG. 14A is a cross-sectional view, from a distal end, of the shaft locking mechanism of FIG. 13A, illustrating a configuration of the shaft locking mechanism in which the shaft is rotated to the right; and FIG. 14B is a cross-sectional view, from a distal end, of the shaft locking mechanism of FIG. 13A, illustrating a configuration of the shaft locking mechanism in which the shaft is rotated to the left.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary devices and methods for calibrating articulating robotic surgical tools are provided.

Figure 1:
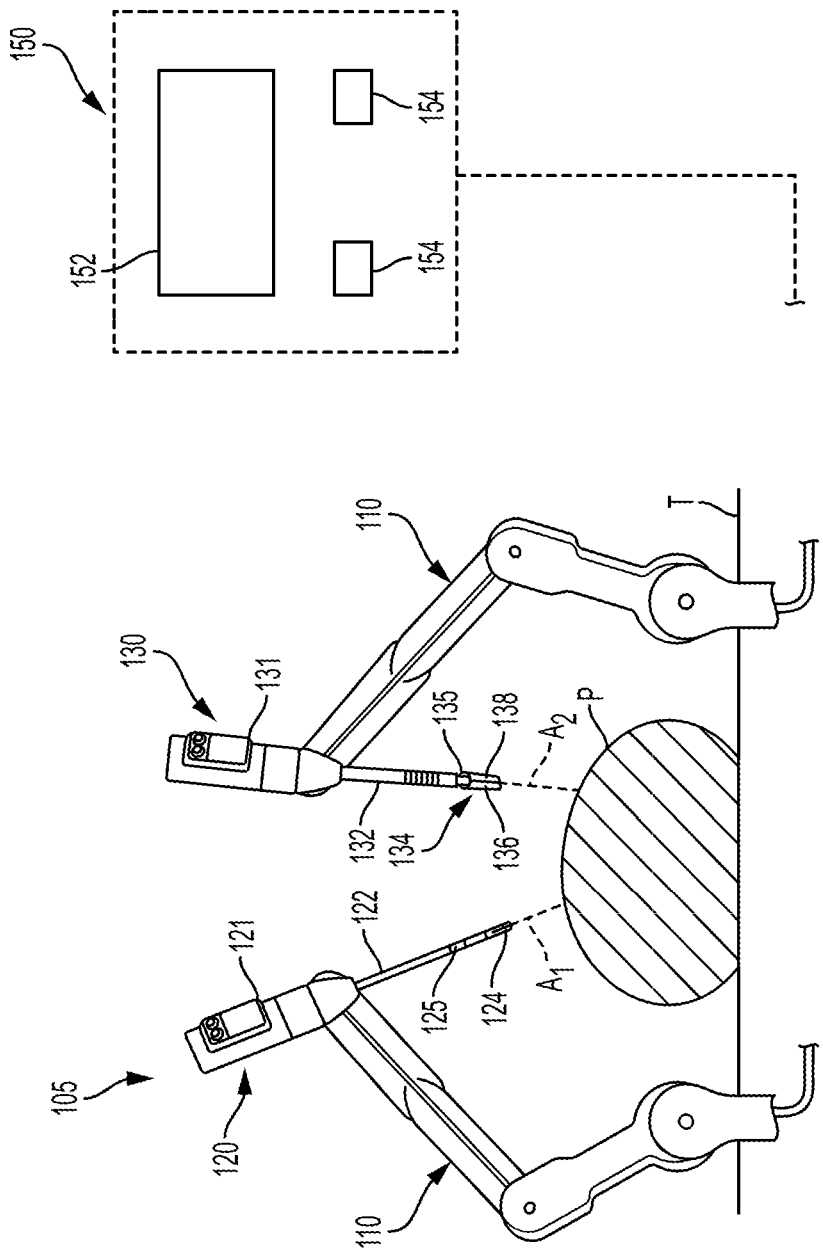
FIG. 1 is a perspective view of one embodiment of a surgical robotic system that includes a patient-side portion and a user-side portion.

FIG. 1 is a perspective view of one embodiment of a robotic surgical system 100 that includes a patient-side portion 105 that is positioned adjacent to a patient P (shown schematically), and a user-side portion 150 that is located a distance from the patient, either in the same room and/or in a remote location. The patient-side portion 105 generally includes one or more robotic arms 110 and one or more tool assemblies or surgical tools 120, 130 that are configured to releasably couple to a robotic arm 110. The user-side portion 105 generally includes a vision system 152 for viewing the patient and/or surgical site, and a control system 154 for controlling the movement of the robotic arms 110 and each surgical tool 120,130 during a surgical procedure.

The control system 154 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 154 can include components that enable a user to view a surgical site of a patient being operated on by the patient-side portion 105 and/or to control one or more parts of the patient-side portion 105 (e.g., to perform a surgical procedure at the surgical site). In some embodiments, the control system 154 can also include one or more manually-operated user input devices, such as a joystick, exoskeletal glove, a powered and gravity-compensated manipulator, or the like. These user input devices can control teleoperated motors which, in turn, control the movement of the surgical system, including the robotic arms 110 and surgical tools 120,130.

The patient-side portion 105 can also have a variety of configurations. As depicted schematically in FIG. 1, the patient-side portion 105 can couple to an operating table T. However, in some embodiments, the patient-side portion 105 can be mounted to a wall, to the ceiling, to the floor, or to other operating room equipment. Further, while the patient-side portion 105 is shown as including two robotic arms 110, more or fewer robotic arms 110 may be included. The robotic arms can be different types of arms. Furthermore, the patient-side portion 105 can include separate robotic arms 110 mounted in various positions, such as relative to the surgical table T (as shown in FIG. 1). Alternatively, the patient-side portion 105 can include a single assembly that includes one or more robotic arms 110 extending therefrom.

Each of the surgical tools 120, 130 can have any suitable configurations, including different configurations from one another. As shown in FIG. 1, the surgical tools 120, 130 include tool housings 121, 131 and elongate shafts 122, 132 extending distally from the respective housings 121, 131. Each of the elongate shafts 122, 132 includes an end effector 124, 132, respectively, coupled to a distal end thereof. The tools can also include a wrist 125, 135 that couples a respective one of the end effectors 124, 134 to the distal end of the shaft 122, 132.

The end effectors 124, 134 are configured to move relative to the shafts 122, 132 at the wrists 125, 135, respectively, e.g., by pivoting at the wrists, to position the end effector at a desired location relative to a surgical site during use of the tool. The housings 121, 131 includes various components (e.g., gears and/or actuators) configured to control the operation various features associated with the end effectors 124, 134 (e.g., any one or more of clamping, firing, rotation, articulation, energy delivery, etc.). In at least some embodiments, one or both of the shafts 122, 132, and hence the end effectors 124, 134 coupled thereto, are configured to rotate about longitudinal axes A1, A2 of the shaft 122, 132, respectively. In such embodiments, the various components of the housing are configured to control the rotational movement of the shaft. In at least some embodiments, as in this illustrated embodiment, each surgical tool 120, 130 is configured to releasably couple to the robotic surgical system 100, and the tool housings 121, 131 can include coupling features configured to allow the releasable coupling of the tools 120, 130 to the robotic surgical system.

A shaft, end effector, wrist, and housing of a surgical tool are discussed further below in connection with the surgical tool 130, though it should be appreciated that the components of the surgical tool 120 can be configured generally in a similar manner.

The surgical tool 130 can have any of a variety of configurations. In general, the surgical tool can be configured to perform at least one surgical function and can include any of, for example, a stapler, a clip applier, forceps, a needle driver, a cautery device, a cutting tool, a pair of jaws, an imaging device (e.g., an endoscope or ultrasound probe), etc. The surgical tool 130 in at least some embodiments is configured to apply energy (such as radiofrequency (RF) energy) to tissue, while in other embodiments the tool 130 is not configured to apply energy to tissue.

The shaft 132 can have any of a variety of configurations. In general, the shaft 132 is an elongate member extending distally from the housing 131 and having at least one inner lumen extending therethrough. The shaft 132 is fixed to the housing 131, but in other embodiment the shaft 132 can be releasably coupled to the housing 131 such that the shaft 132 can be interchangeable with other shafts. This may allow a single housing 131 to be adaptable to various shafts having different end effectors.

The end effector 134 can have a variety of sizes, shapes, and configurations. For example, the end effector 134 can be or can include a tissue grasper having a pair of opposed jaws 136, 138 configured to move between open and closed positions with one or both of the jaws 136, 138 configured to pivot at the wrist 135 to move the end effector 134 between the open and closed positions. The end effector 134 in other embodiments can have other configurations, e.g., scissors, a babcock, a retractor, etc. The wrist 135 can have any of a variety of configurations. In general, the wrist 135 can include a joint configured to allow movement of the end effector 134 relative to the shaft 132, such as a pivot joint at which the jaws 136, 138 are pivotally attached.

Figure 2:
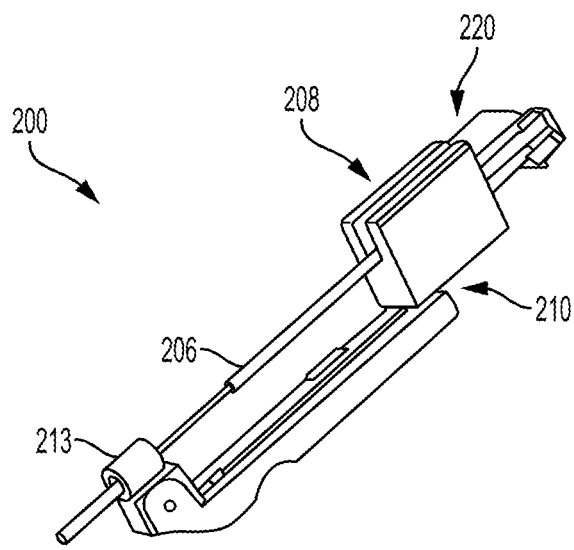
FIG. 2 is a perspective view of a surgical tool coupled to a tool driver of a robotic surgical system.

FIG. 2 illustrates an example of a robotic arm 210 and a tool assembly or surgical tool 220 (partially shown) releasably coupled to the robotic arm 210 of a robotic surgical system 200. The robotic arm 210 can be an electromechanical and it includes a tool driver 208 configured to releasably mate with the surgical tool 220. The robotic arm 210 can support and move the associated surgical tool 220 along one or more mechanical degrees of freedom (e.g., all six Cartesian degrees of freedom, five or fewer Cartesian degrees of freedom, etc.).

The tool driver 208 is configured to assist with controlling features associated with the surgical tool 220. Although not shown in FIG. 2, the tool driver 208 can include one or more motors with shafts that either rotate or translate, and that couple to the surgical tool to effect motion of various components of the surgical tool. The robotic arm 210 can also include an entry guide 213 (e.g., a cannula mount, cannula, a trocar holding feature, or other suitable component) that can be a part of or removably coupled to the robotic arm 210, as shown in FIG. 2.

The surgical tool 220 can be inserted proximally through the driver 208 and the cannula for insertion into a patient. Thus, FIG. 2 illustrates an elongate shaft 206 of the surgical tool 220 extending distally from the tool driver 208 when the tool 220 is coupled to the driver 208. It should be appreciated that the configuration of the robotic arm can vary, and that the surgical tools described herein can be used with any suitable robotic arm.

In order to provide a sterile operation area while using the surgical system, a barrier (not shown) can be placed between the actuating portion of the surgical system (e.g., the robotic arm 210) and the surgical instruments (e.g., the surgical tool 220). A sterile component, such as a sterile barrier or an instrument sterile adapter (ISA) (not shown), can also be placed at the connecting interface between the surgical tool 220 and the robotic arm 210. The placement of an ISA between the surgical tool 220 and the robotic arm 210 can ensure a sterile coupling point for the surgical tool 220 and the robotic arm 210. This permits removal of the surgical tool 220 from the robotic arm 210 to exchange with other surgical tools during the course of a surgery without compromising the sterile surgical field.

Figure 3:
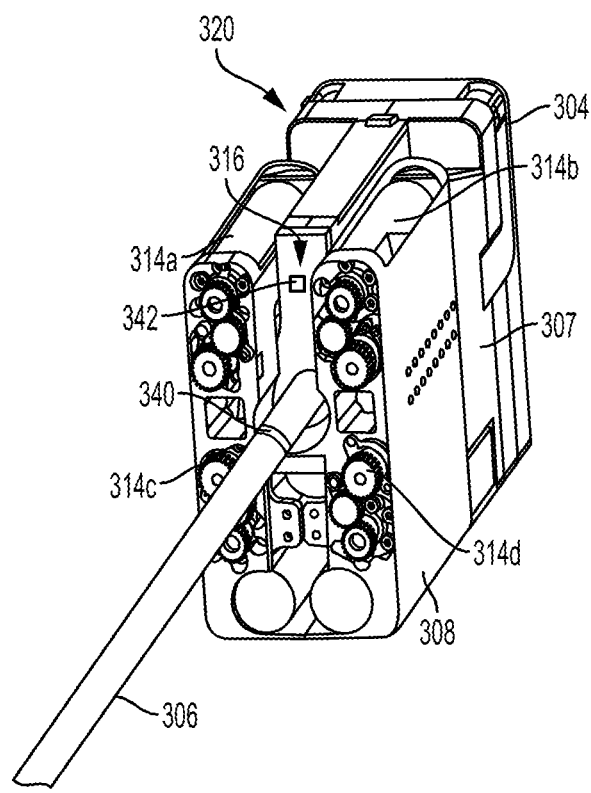
FIG. 3 is another perspective view of a surgical tool coupled to a tool driver of a robotic surgical system.

FIG. 3 illustrates an example of a tool driver 308 of an electromechanical arm of a robotic surgical system in more detail. The driver 308 can be, for example, similar to tool driver 208 (FIG. 2), or it can have any other configuration. In FIG. 3, the tool driver 308 is shown to have a tool housing 304 of a surgical tool 320 to be releasably coupled thereto, with an elongate shaft 306 of the tool 320 extending distally from the tool housing 304 and the tool driver 308. The shaft 306 has an end effector (not shown) coupled to a distal end thereof, such as, e.g., any of the end effectors 124, 134 (FIG. 1) or any other end effectors. Only a partial portion of the robotic surgical system is shown in FIG. 3 for clarity of illustration. Also, in this example, a sterile barrier 307 is disposed between the tool driver 308 and the tool housing 304. However, it should be appreciated that the sterile barrier 307 is shown by way of example only, as a sterile barrier between the tool and the tool driver can have any suitable configuration.

As shown in FIG. 3, the tool driver 308 can include one or more motors, e.g., four motors 314a-314d are shown, that control a variety of movements and actions associated with the tool 320. For example, each motor 314a-314d can couple to and/or interact with a coupling or activation feature (e.g., gear) associated with the surgical tool 320 for controlling one or more actions and movements that can be performed by the surgical tool 320, such as for assisting with performing a surgical operation. The motors 314a-314d can be accessible on an upper surface of the tool driver 308, and thus the surgical tool 320 can be configured to mount on top of the tool driver 308 to couple thereto. As shown in FIG. 3, the tool driver 308 can also include a shaft-receiving channel 316 formed in a sidewall thereof for receiving the shaft 306 of the surgical tool 320. In other embodiments, additionally or alternatively, the shaft can extend through an opening in the tool driver 308, or the two components can mate in various other configurations.

The tool housing 304 can include coupling features that assist with releasably coupling the housing 304 to the tool driver 308 of the robotic arm 110. The housing 304 can include gears and/or actuators that can be actuated by the one or more motors 314a-314d in the driver 308. The gears and/or actuators in the housing 304 can control the operation of various features associated the end effector coupled to the shaft 306 (e.g., clamping, firing, rotation, articulation, etc.), as well as control the movement of the shaft 306, such as rotation of the shaft. The shaft 306 can include actuators and connectors that extend along the shaft and assist with controlling the actuation and/or movement of the end effector (e.g., opening and closing of the jaws) and/or shaft 306.

In some exemplary embodiments, the housing 304 can have at least one rotary input coupling and at least one linear input coupling for allowing either a rotary output or a linear output from the tool driver 308 to activate at least one mechanism of the surgical tool 320. For example, the at least one mechanism of the surgical tool can include one or more of a clamping assembly, a firing assembly, an articulation assembly, and a rotation/roll assembly. The clamping assembly can be configured to cause opening and closing of the opposed jaws of the end effector. The firing assembly can be configured to cause an I-beam to translate through the end effector for firing staples and cutting tissue. In other embodiments, the firing assembly can cause energy delivery, or other actions to occur depending on the configuration of the end effector. The articulation assembly can be configured to cause the end effector to articulate relative to the elongate shaft. The roll assembly can be configured to cause the elongate shaft and end effector to rotate about a longitudinal axis of the elongate shaft. In some embodiments, a single rotary input and/or linear input can control more than one of these mechanisms.

As discussed above, a surgical tool can be coupled to an electromechanical arm of a robotic surgical system and an elongate shaft of the tool can be configured to be rotated to thereby rotate an end effector coupled distally to the shaft. In some embodiments, the tool's shaft can rotate at least 360 degrees. The elongate shaft can rotate with respect to its longitudinal axis and the rotation angle of the shaft can be measured by the surgical system with respect to a certain reference or "zero-angle" position of the shaft, which can be an absolute or relative zero-angle position. To enable accurate control of movements of the end effector during a surgical procedure, the robotic surgical system must often be able to determine a rotation angle of the shaft when the shaft is installed on the system. In particular, when the surgical tool is connected to the driver, the system needs to calibrate the shaft to know a rotational angle of the shaft.

In this way, the surgical system can effectuate a more precise control over rotation of the end effector during a surgical procedure. In some instances, when the tool and thus its shaft are disconnected from a tool driver of the electromechanical arm and then returned to the driver, the surgical system needs to be able to determine a rotational angle of the shaft to return the shaft to a position prior to its removal and/or to control the shaft in a desired manner.

Accordingly, in some embodiments, methods and systems for determining an angle of rotation of an elongate shaft of a surgical tool are provided. The surgical tool can be configured to be removably coupled to an electromechanical arm of a robotic surgical system. A suitable assembly (e.g., a roll assembly associated with the electromechanical arm), can be configured to cause the elongate shaft and an end effector coupled to a distal end thereof to rotate about a longitudinal axis of the elongate shaft. The surgical tool can be coupled to a tool driver of the electromechanical arm, and the driver can have one or more rotary input mechanisms configured to cause the shaft of the tool to rotate when the tool is coupled to the arm. Determining the rotation angle of the shaft allows controlling operation of the end effector in a desired manner.

In the described embodiments, a rotation angle of the shaft can be determined using at least one target associated with the shaft and at least one sensor configured to detect a position of the target. The target can be an element that is associated with the shaft and non-independently movable with respect to the shaft. The at least one sensor configured to detect a position of the target can be disposed such that the shaft moves independently of the sensor. The sensor can sense a position of the target by detecting a position of a predetermined point on the target or by detecting various points on the target. To detect the position, one or more sensors can measure one or more parameters (e.g., magnetic field, light absorption or reflections, etc.) at one or more rotational positions of the shaft and to output a corresponding voltage. The detected position of one or more points of the target is then used to determine a rotation angle of the shaft, as discussed in more detail below.

The target can be associated with the shaft in a variety of different ways. For example, it can be coupled to the shaft. Additionally or alternatively, the target can be in the form of one or more portions of the shaft, which can have one or more properties distinct from a remainder of the shaft. The target can be disposed closer to a proximal end of the shaft. The sensor can be disposed at a suitable location such that the shaft is able to move independently of the sensor. For example, the sensor can be disposed on an electromechanical arm of the robotic system, such as, for example, on a tool driver. For example, with reference to FIG. 3, a target 340 (shown schematically) can be disposed on the shaft 306 such that at least one sensor 342 (also shown schematically) can sense a position of the target 340. The sensor can be remote from the shaft. For example, as schematically shown in FIG. 3, the sensor 342 can be mounted on the shaft-receiving channel 316 of the tool driver 308. Also, the sensor can be mounted on a trocar or another component of the electromechanical arm. Furthermore, in some cases, the sensor can be disposed on the tool (e.g., on a tool housing).

Figure 4:
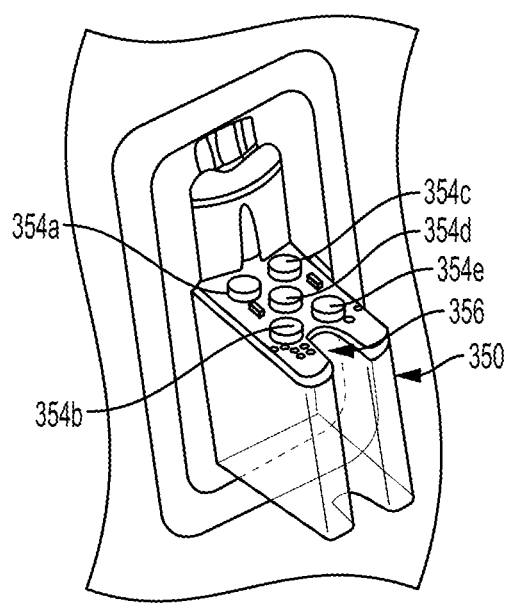
FIG. 4 is perspective view of a tool driver of a robotic surgical system.

FIG. 4 additionally illustrates another example of a tool driver 350 of a robotic surgical system having a shaft-receiving channel 356 for receiving a shaft of a surgical tool (not shown). The shaft-receiving channel 356 can seat therein one or more sensors configured to detect a position of the target associated with the shaft. As shown, the tool driver 350 includes one or more motors, e.g., five motors 354a-354e are shown, that control a variety of movements and actions associated with the tool coupled to the tool driver 350. For example, each motor 354 can couple to and/or interact with an activation feature (e.g., gear) associated with the tool for controlling one or more actions and movements that can be performed by the tool, such as for assisting with performing a surgical operation. The tool is configured to mount on top of the tool driver 350 to couple thereto.

The sensor can detect a position of the target in various ways. The sensor can sense various parameters, a type of which depends on the type of the target and the sensor. For example, the sensor can be in the form of one or more Hall Effect sensors configured to sense changes in the target movement. The sensor can also be an optical sensor, inductance sensor, or any other type of sensor. Regardless of the specific configurations of the target and sensor, they are used to establish a rotational angle of the shaft during initialization of the surgical tool. The sensors are thus used for the tool shaft calibration process. Additionally, in some embodiments, they can be used in addition to motor rotation sensors of the tool, in circumstances when it is required to verify operation of the motor rotation sensors.

In the embodiments discussed below, for illustration purposes, only a portion of an elongate shaft of a surgical tool is shown in the various figures. It should be appreciated that the elongate shaft can be part of any surgical tool that is configured to be removably coupled to an electromechanical arm of a robotic surgical system such that the shaft is rotatable about is longitudinal axis. For example, the shaft can be part of any of the tools 120, 130 (FIG. 1), tool 220 (FIG. 2), tool 320 (FIG. 3), or any other suitable surgical tool.

Figure 5A:
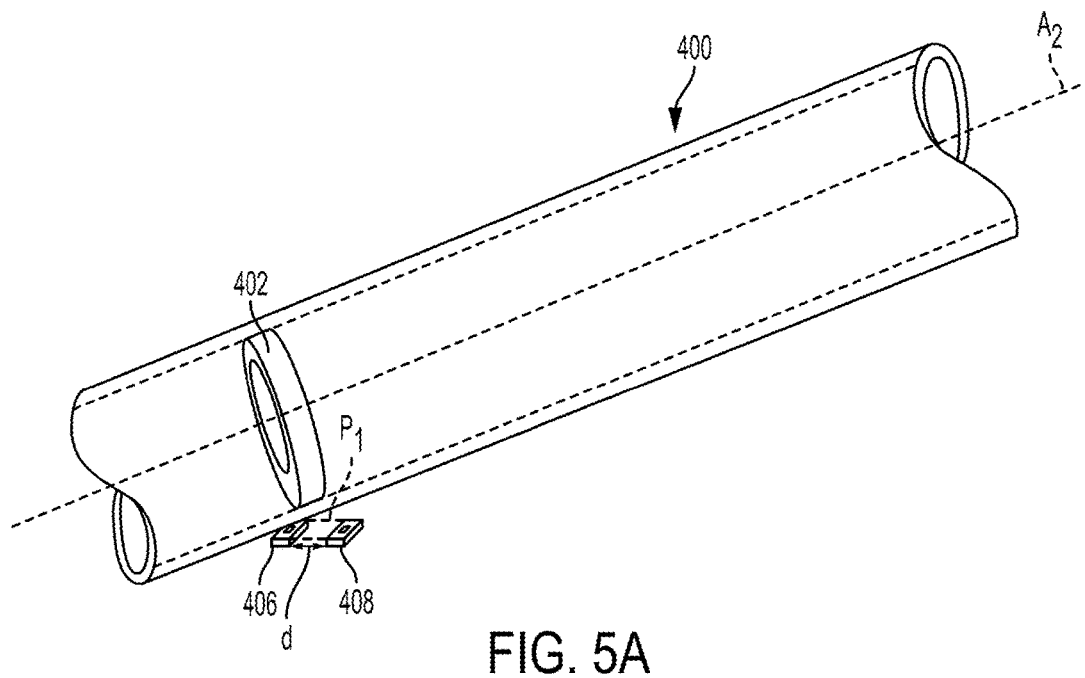
FIG. 5A is a perspective, partially transparent view of a shaft of a surgical tool having a target associated therewith, showing the target that is coupled to the shaft.
Figure 5B:
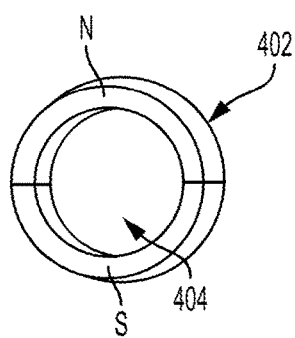
FIG. 5B is a schematic illustration of the target of FIG. 5A.

In some embodiments, the target is at least one substantially circular magnetic feature associated with an elongate shaft of a surgical tool. FIGS. 5A and 5B illustrate an embodiment of an elongate shaft 400 of a surgical tool having a target in the form of a substantially circular magnetic feature 402 disposed in the shaft 400 coaxially therewith. As shown in FIG. 5B, the magnetic feature 402 is a generally circular, ring-like element having a large central opening 404. As shown in FIG. 5A, the magnetic feature 402 is disposed in the shaft 400 coaxially therewith such that a longitudinal axis of the magnetic feature 402 (not shown separately) coincides with a longitudinal axis A2 of the shaft 400.

The magnetic feature 402 can be a diametrically magnetized ring-like feature such that it has a "north" portion (N) on one half and an opposite "south" (S) portion, as schematically shown in FIG. 5B. The magnetic feature 402 can be coupled to interior walls of the shaft 400 in any suitable manner and/or using any suitable attachment feature. For example, the magnetic feature 402 can be embedded in the shaft 400.

In this embodiment, the position of the magnetic feature 402 can be sensed using first and second sensors 406, 408 disposed in the plane P1. The sensors 406, 408 can be suitable non-contact position sensors such as, for example, Hall Effect sensors disposed at a suitable location adjacent to the target magnetic feature 402. For example, the sensors 406, 408 can be disposed on the tool driver. However, in some implementations, the sensors 406, 408 can be disposed on the surgical tool. Regardless of their specific locations, the shaft 400 is movable independently of the sensors 406, 408.

In the example illustrated, the first and second sensors 406, 408 are disposed in the same plane P1 at a certain distance d from one another. The first and second sensors 406, 408 are adjacent to the shaft 400, and the plane P1 is perpendicular to the longitudinal axis A2 of the shaft 400.

Figure 5C:
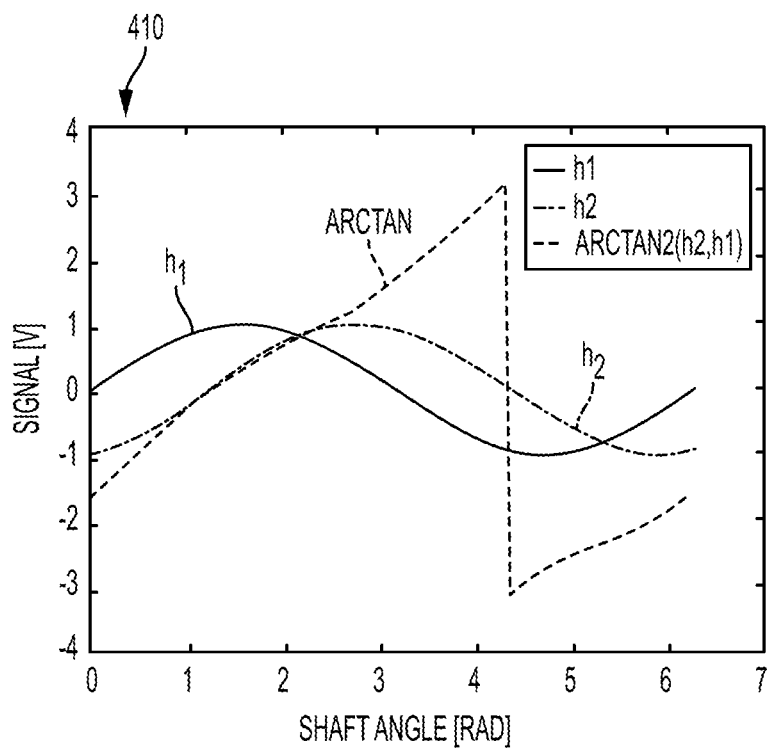
FIG. 5C is a schematic illustration of graphs constructed using values obtained during calibration of the shaft of FIG. 5A.

The first and second sensors 406, 408 are configured to sense voltage indicating a position of the magnetic feature 402 and therefore a position of the shaft 400. The first and second sensors 406, 408 together can sense 360 degrees of rotation and are used to determine an absolute position of the shaft 400. As the position of the magnetic feature 402 changes with rotation of the shaft 400, each of the first and second sensors 406, 408 senses the magnetic vector of the field from the magnetic feature 402 and generates voltage (V) signals that are proportional to sine waves. Because the sensors 406, 408 are in the same plane P1, but are separated by some distance d, the voltage measured by sensors 406, 408 traces sine waves with a phase separation. For example, FIG. 5C illustrates a graph 410 showing a curve H1 representing voltage signals measured by the first sensor 406 as a function of a rotational angle (in radians) of the shaft 400 and a curve H2 representing voltage signals measured by the second sensor 408 as a function of a rotational angle (in radians) of the shaft 400.

Information sensed by the sensors 406, 408 can be transmitted to a suitable computing system for processing. For example, the voltages sensed by the sensors 406, 408 are used to calculate the arctangent or arctan of the voltages that is, in turn, used to determine an (absolute) angle of the shaft. Thus, FIG. 5C illustrates a curve Arctan representing the arctan as a function of an absolute rotation angle of the shaft 400 (in radians).

A suitable processor can be used to calculate the arctan. For example, the voltages sensed by the sensors 406, 408 can be transmitted to a computing system (e.g., computer system shown in FIG. 12A), which can be associated with the surgical system in any suitable manner (e.g., the computer system can be remote), and the processor can calculate the arctan of the voltages. The arctan can be compared to calibration values to determine the angle of the shaft. For example, a suitable non-volatile memory (which can be located in the tool or at a suitable location at the robotic surgical system) can store arctan values and corresponding rotational angles of a shaft. An example of such memory that can be disposed on the surgical tool is shown in FIG. 12B. The computing system can access such memory and compare the calculated arctan to previously stored arctan values to identify a matching arctan value, and to determine a rotational angle of the shaft based on a stored value of a rotation angle corresponding to the matching arctan value.

Figure 5D:
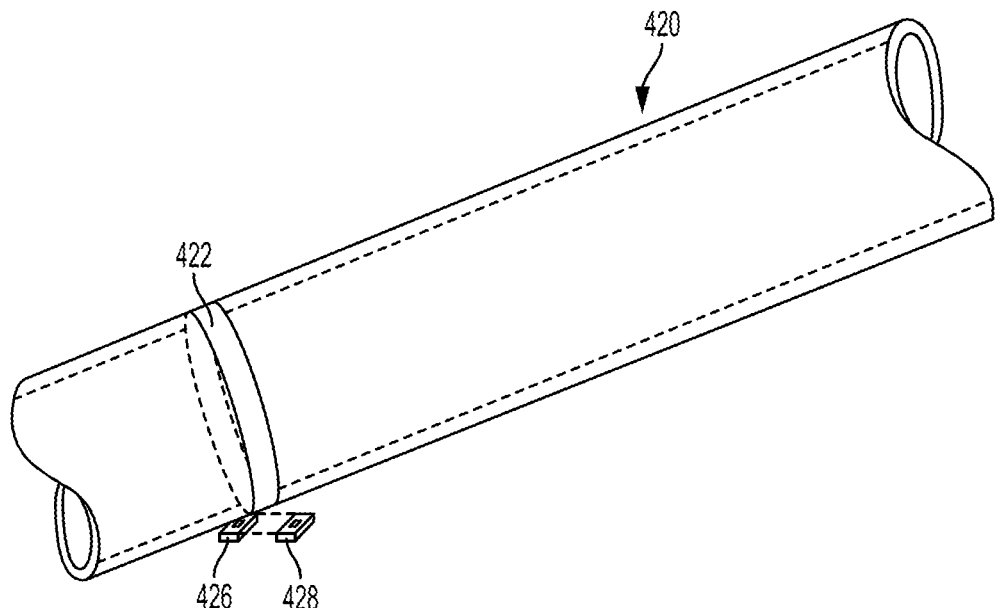
FIG. 5D is another perspective, partially transparent view of a shaft of a surgical tool having a target associated therewith, showing the target that is formed from a portion of the shaft.

In some embodiments, the shaft of a surgical tool can have at least one portion that is magnetized and disposed at least partially along a circumference of the shaft. FIG. 5D illustrates an example of a shaft 420 of a surgical tool having a target in the form of at least one magnetized portion 422 that is disposed at least partially along a circumference of the shaft Like the position of magnetic feature 402 (FIGS. 5A and 5B), the position of the magnetized portion 422 is detected using first and second sensors 426, 428, which can be similar to first and second sensors 406, 408 (FIG. 5A). The rotation angle of the shaft 420 can be determined in a manner similar to the technique described above in connection with FIG. 5C.

In the examples shown in FIGS. 5A and 5D, because the sensors 406, 408, 426, 428 measure magnetic field, they can be disposed on a tool driver or on the tool. The sensors 406, 408, 426, 428 are "absolute," meaning that each position of the shaft corresponds to a respective unique angle of the shaft. Thus, the rotation angle of the shaft can be determined without the need to rotate of the shaft when it is coupled to the tool driver.

In some embodiments, one or more portions of a surface of an elongate shaft of a surgical tool can have properties that allow those portions to be used as a target for at least one sensor. In this way, at least one target can be in the form of at least one portion of the shaft that is disposed at least partially along a circumference of the shaft. The portion can have at least one light absorption property that is different from at least one light absorption property of a remainder of the shaft. In such embodiments, the sensor can be in the form of a transmitter and a receiver.

For example, the surface of the shaft can be treated such that some regions absorb or refract most light, and some regions reflect most light. Non-limiting examples of absorptive/refractive treatment include surface etching and powder coat with matte black or bead blasting. Non-limiting examples of reflective treatment include polishing, coating with chrome, aluminum, or other metal, and embedding the surface with glass particles. Any other suitable techniques can be used additionally or alternatively.

Figure 6A:
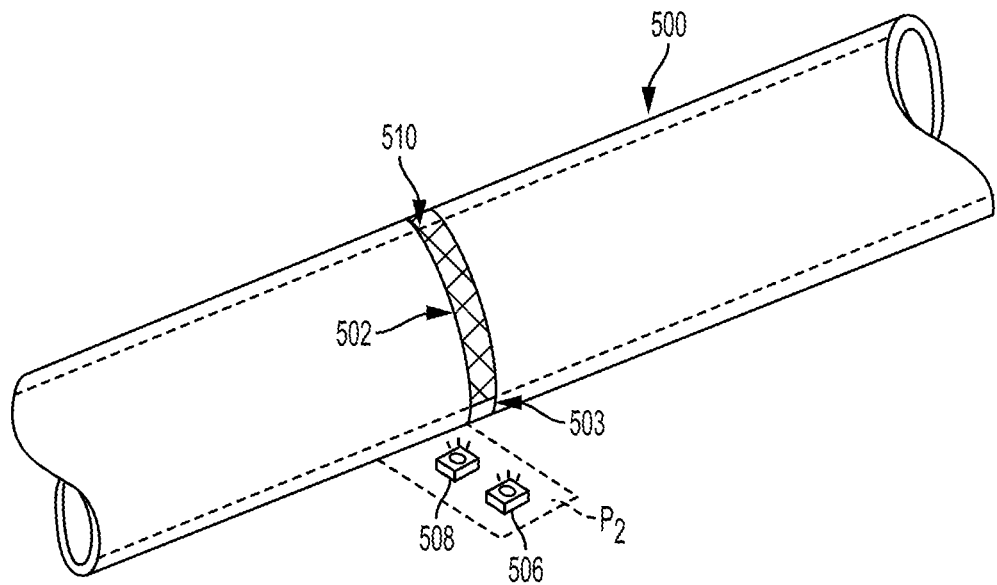
FIG. 6A is a perspective view of a shaft of a surgical tool having a target associated therewith.

FIG. 6A illustrates an embodiment of a shaft 500 of a surgical tool having a target in the form of a portion of the shaft 500 forming a band 510 that is disposed at least partially along a circumference of the shaft. The sensors include an optical transmitter 506 and an optical receiver 508. The band 510 includes an absorptive portion 502 and a smaller portion 503 that is reflective. The band 510 can have a uniform width along its length extending along the circumference of the shaft 500. In this example, the reflective portion 503 can be in the form of a discrete portion having the same width as the rest of the band 510. The length of the reflective portion 503 can span, for example, about 5% of the length of the band. However, the portion 503 can have another length selected such that the optical receiver 508 can detect it. For example, the length of the reflective portion 503 can span a portion of the band 510 that is from about 1% to about 10% of the length of the band, or any other band's portion that allows detecting the reflective portion 503.

The optical transmitter and receiver 506, 508 can be disposed in the same plane P2 in which at least a part of the band 510, which includes the portions 502, 503, is disposed. In this embodiment, in use, upon initialization of the surgical tool, the robotic system activates the transmitter and receiver 506, 508, and causes the shaft 500 to rotate until light transmitted by the transmitter 506 is reflected by the reflective portion 503 of the band 510, which is detected by the receiver 508. At that point, it can be detected that the position of the shaft corresponds to its zero rotation angle. After the shaft is calibrated in this manner, the robotic surgical system can control operation of the shaft such that the shaft can be rotated to desired angles. If the tool is disconnected from the tool driver and then reconnected with the tool driver, the shaft can again be calibrated in the described manner.

Figure 6B:
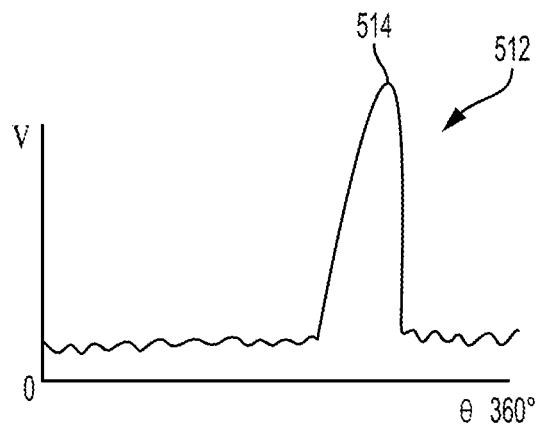
FIG. 6B is a schematic illustration of a graph illustrating calibration values for shaft of FIG. 6A.

FIG. 6B shows a graph 512 schematically illustrating calibration data that can be acquired during a process of calibrating the shaft 500. In particular, the graph 512 illustrates voltage (V) sensed by the receiver 508 as a function of an angle (θ) of the shaft. The shaft 500 is rotated from an initial rotation angle (which may not be a position at which the angle is taken to be a zero, and which is not initially not known to the robotic system) until a spike 514 in the voltage sensed by the receiver 508 is detected. In the example illustrated, the spike corresponds to the detection of the reflective portion 503 by the receiver 508.

In some embodiments in which optical sensors are used to detect a rotation angle of the shaft, a target associated with the shaft can be configured such that each angle of the shaft corresponds to unique amount of light that is acquired by an optical receiver. Thus, in such embodiments, the rotation angle of the shaft can be measured when the shaft is connected to a tool driver, without the need to rotate the shaft.

Figure 7A:
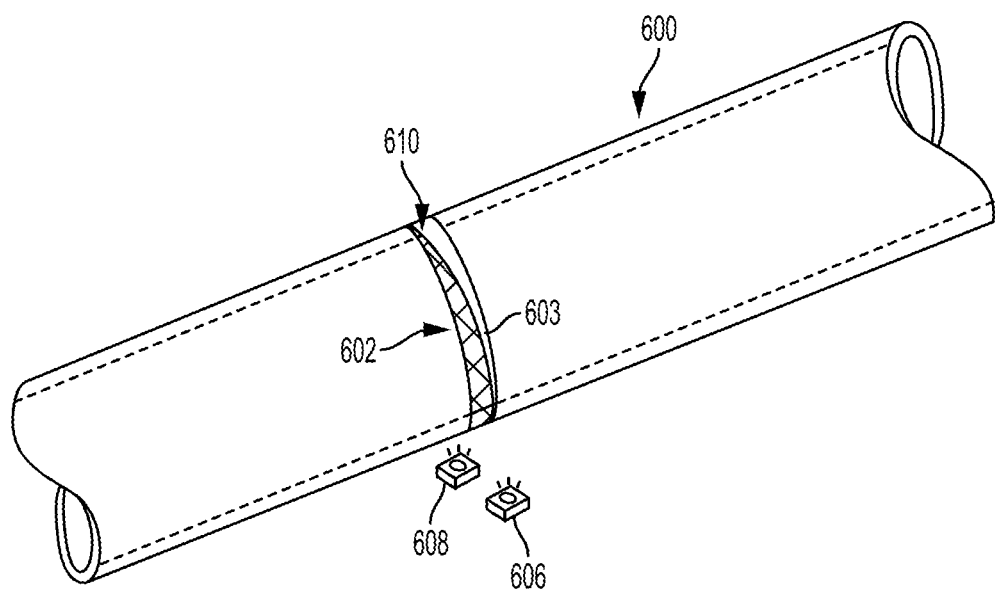
FIG. 7A is another perspective view of a shaft of a surgical tool having a target associated therewith.

FIG. 7A illustrates an embodiment of a shaft 600 of a surgical tool having a target in the form of a portion of the shaft 600 forming a band 610 that is disposed at least partially along a circumference of the shaft. Similar to the embodiment shown in connection with FIG. 6A, the sensors include an optical transmitter 606 and an optical receiver 608. The band 610 includes an absorptive portion 602 and a reflective portion 603. The band 610 can have a uniform width along its length extending along the circumference of the shaft 600. In this example, the absorptive and reflective portions 602, 603 are shaped as wedges having the same or different lengths that are wrapped around the shaft 600 to form the band 610. The wedges can be configured as portions having a gradually reducing thickness, such that the thickness of the absorptive and reflective portions 602, 603 is reduced in opposite directions. In this way, an end of the absorptive portion 602 having the largest width is disposed adjacent to an end of the reflective portion 603 having the smallest width, and vice versa. It should be appreciated, however, that the absorptive and reflective portions 602, 603 can be formed within the band 610 in any suitable manner that allows different amount of light to be detected by the receiver 608 depending on a rotation angle of the shaft.

Figure 7B:
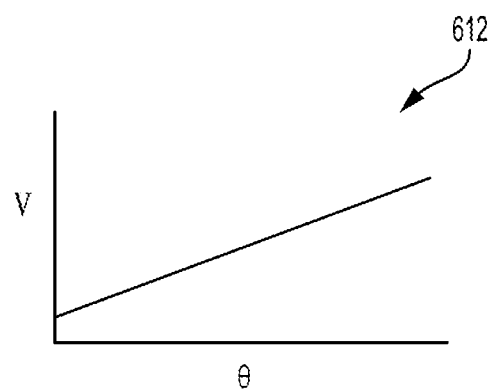
FIG. 7B is a schematic illustration of a graph illustrating calibration values for the shaft of FIG. 7A.

FIG. 7B illustrates a graph 612 schematically illustrating dependency of voltage (V) sensed by the receiver 608 from a rotation angle (θ) of the shaft. As shown, each angle corresponds to a respective unique voltage. During assembly of the tool having the shaft 600, the voltage and corresponding shaft rotation angle values can be recorded in a suitable memory, such as in a memory on the tool.

Figure 8A:
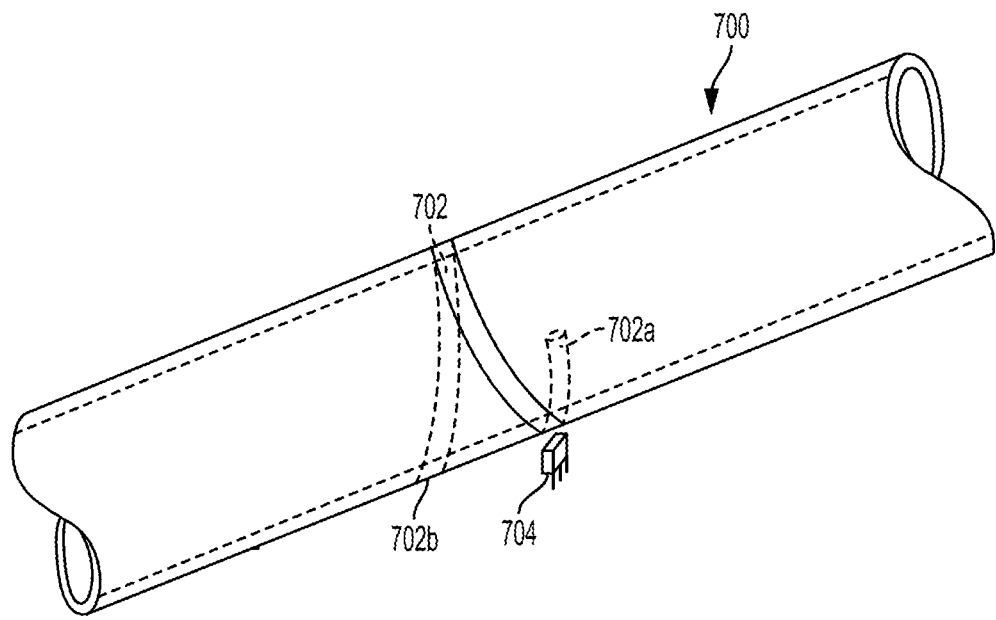
FIG. 8A is yet another perspective view of a shaft of a surgical tool having a target associated therewith.

FIG. 8A illustrates another embodiment of a shaft 700 of a surgical tool where a rotation angle of the shaft can be measured. As shown, in this example, a target is in the form of an elongate magnetic element 702 having first and second ends 702a, 702b and disposed substantially helically around the shaft 700. The position of the magnetic element 702 can be detected using a sensor 704.

The magnetic element 702 can have various suitable configurations. For example, as shown in FIG. 8A, it can be a thin magnetic strip having a substantially uniform width and thickness throughout its length. The magnetic element 702 can be a separate element coupled to the outer wall of the shaft 700 in a suitable manner (e.g., bonded). Alternatively, the magnetic element 702 can be formed by magnetizing the material of the shaft in the shape of a helix. Also, in at least one embodiment, the magnetic element 702 can also be formed as a combination of magnetic elements coupled to the shaft and magnetized portions of the shaft.

Figure 8B:
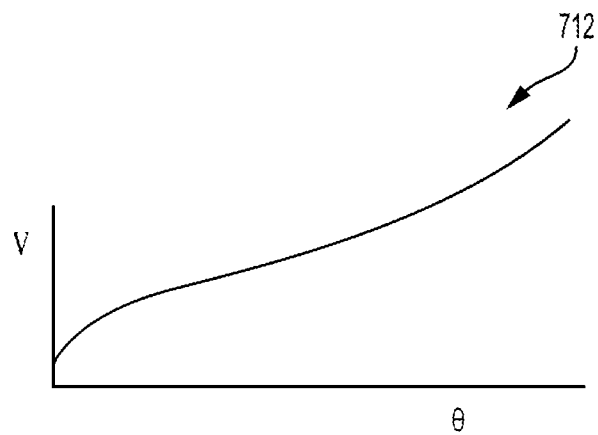
FIG. 8B is a schematic illustration of a graph illustrating calibration values for the shaft of FIG. 8A.

The sensor 704, which can be disposed on a tool driver configured to couple with the tool, is disposed adjacent to one of the first and second ends 702a, 702b of the magnetic element 702. The sensor 704 can be, for example, a Hall Effect sensor. As the shaft 700 rotates, the portion of the magnetic element 702 that is closest to the sensor 704 creates a measurable voltage proportional to the magnetic field and therefore related to the distance between the sensor 704 and the magnetic element 702. Since the magnetic element 702 is wrapped around the shaft 700 so as to form a helix, the sensor-facing side effectively translates relative to the sensor 704 as the shaft 700 rotates. In this way, the sensor 704 senses a unique voltage for every angle of the shaft 700, as illustrated in a graph 712 in FIG. 8B.

In some embodiments, at least one target is in the form of one or more magnets disposed at a predetermined position along a shaft of a surgical tool and offset from a central longitudinal axis of the shaft.

Figure 9A:
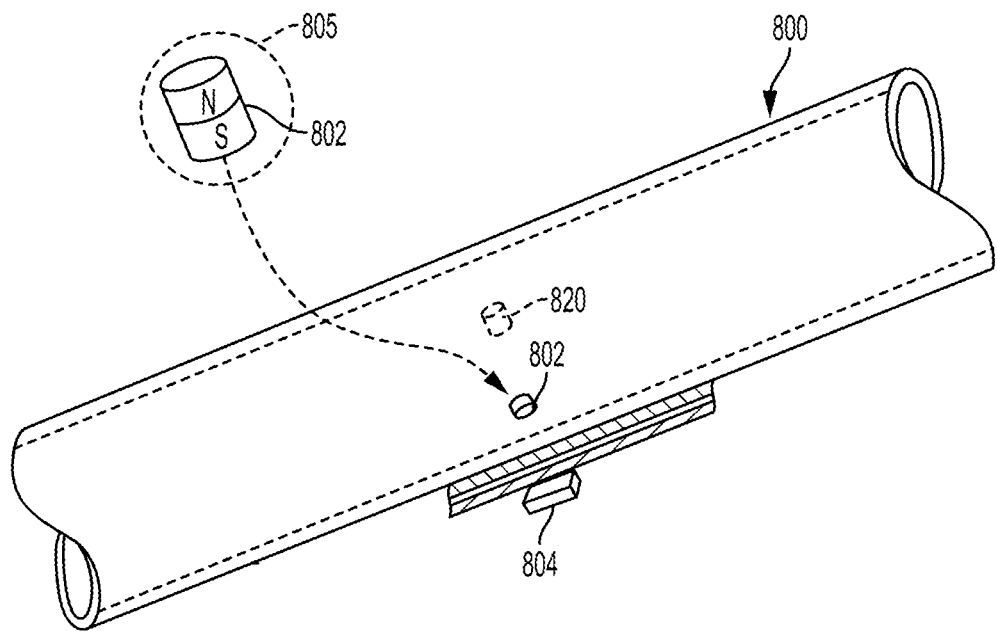
FIG. 9A is yet another perspective view of a shaft of a surgical tool having a target associated therewith.

FIG. 9A illustrates an embodiment of a shaft 800 of a surgical tool of a robotic surgical system that has one or more magnets coupled thereto. In this example, a magnet 802 (an enlarged view of which is also shown in an inset 805) is disposed at a predetermined location at the shaft 800 such that the field of the magnet 802 is oriented radially. A sensor 804, such as, for example, a Hall Effect sensor, is disposed adjacent to the shaft 800 to detect the magnet 802, as shown in FIG. 8A.

Figure 9B:
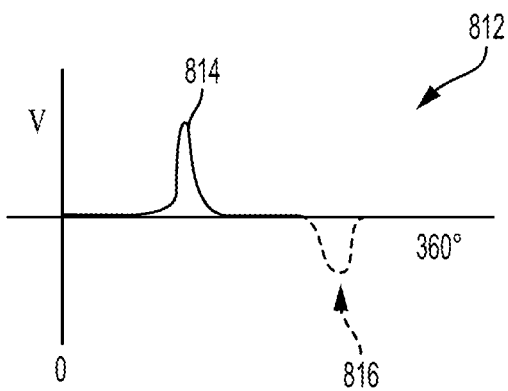
FIG. 9B is a schematic illustration of a graph illustrating calibration values for the shaft of FIG. 9A.

The magnet 802 can have various suitable configurations. For example, it can be a generally cylindrical magnet having a diameter that is much smaller than a diameter of the shaft 800. In this way, the sensor 804 detects the magnet 802 when the magnet 802 is at a certain distance therefrom, which corresponds to a zero-angle position of the shaft. Thus, to determine the zero-angle position of the shaft when the tool with the shaft is coupled to the robotic surgical system, during the calibration process, the system causes the shaft 800 to rotate until the magnet 802 is detected. A graph 812 in FIG. 9B illustrates schematically voltage detected by the sensor 804 as the shaft 800 rotates during the calibration. As shown, a spike 814 in voltage V is sensed by the sensor 804 when the magnet 802 disposed on the shaft 800 is detected. The position of the shaft 800 at which the magnet 802 is detected corresponds to the zero-angle position, which can be determined by comparing the sensed voltage to voltage values stored in a database or other suitable storage in association with respective shaft rotation angle positions.

In some embodiments, another magnet 820 can be used in addition to the magnet 802, as shown schematically in FIG. 9A. The magnet 820, which is disposed at a predetermined location on the outer wall of the shaft 800, can be similar to the magnet 802 such that it can be a relatively small, generally cylindrical magnet. The magnets 802, 820 are oriented with the opposite poles facing the center of the shaft 800. In this way, the degree by which the shaft 800 must rotate during calibration to move to its zero-angle position is reduced. In particular, when a south-facing magnet is closer to the sensor 804, a voltage drop is detected when that magnet passes the sensor 804 (as shown by a "negative" spike 816 in FIG. 9B). When the north-facing magnet is closer to the sensor 804, a voltage rise is detected as shown by the spike 814 in FIG. 9B.

In some embodiments, at least one target is in the form of at least one substantially circular conductive feature disposed around a circumference of a shaft of a surgical tool, and at least one sensor can be an inductive sensor. In such embodiments, the shaft angle is determined based on sensing the inductance of a certain portion of the shaft.

Figure 10A:
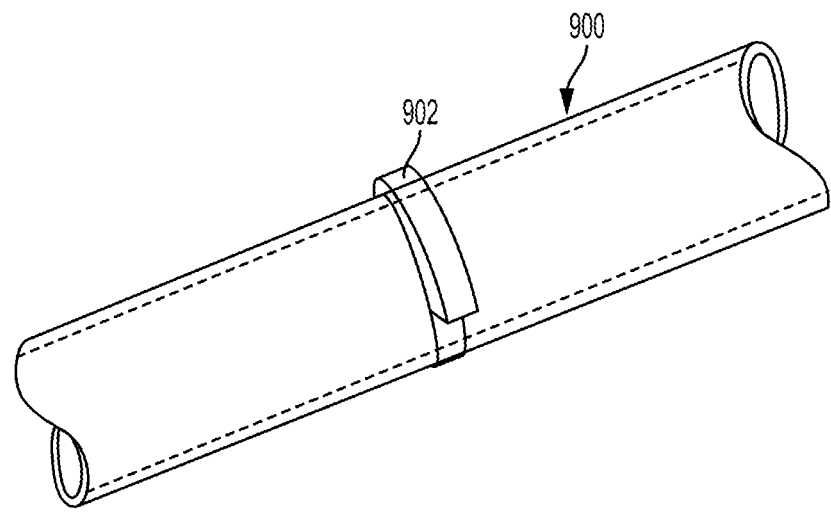
FIG. 10A is yet another perspective view of a shaft of a surgical tool having a target associated therewith.
Figure 10B:
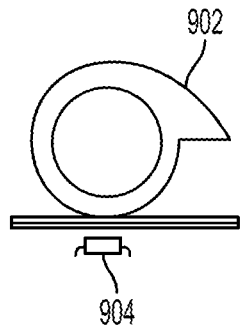
FIG. 10B is a schematic illustration of the target of FIG. 10A and a sensor configured to detect position of the target.

FIGS. 10A and 10B illustrate an embodiment of the shaft 900 including a conductive feature 902 disposed around a circumference of the shaft 900. In this example, the conductive feature 902 is shaped such that its thickness changes along its length (the length is measured along the circumference of the shaft 900), as shown in FIGS. 10A and 10B. Thus, outer walls of the conductive feature 902 form a linear spiral extending over the shaft 900.

As shown schematically in FIG. 10B, an inductance sensor 904 is disposed adjacent to the conductive feature 902. The sensor 904 can be disposed on an electromechanical arm of a robotic surgical system, e.g., on a tool driver configured to be coupled with the tool. The sensor 904 can also be disposed on another component of the electromechanical arm, such as on a trocar holder. Also, in some embodiments, the sensor can be disposed on the tool.

Figure 10C:
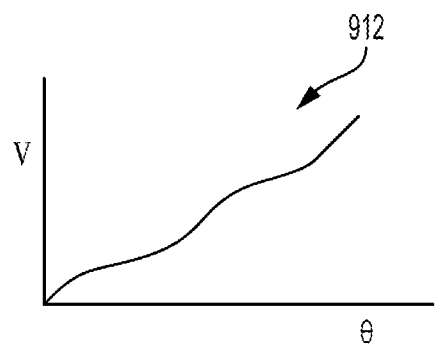
FIG. 10C is a schematic illustration of a graph illustrating calibration values for the shaft of FIG. 10A.

The asymmetric shape of the spiral-like conductive feature 902 is used to "assign" a unique distance value to each angle on the tool shaft 900. Different amounts of material of the feature 902 are associated with different rotation angles. The strength of the inductance between the conductive target and the sensor coil varies as a point on the conductive feature 902 is rotated as the shaft 900 rotates. Rotation of the shaft 900 changes the distance between the surface of the conductive feature 902 and the sensor 904, such that a unique voltage reading on the sensor 904 corresponds to each shaft angle. In this way, the sensor 904 senses a unique voltage for every angle of the shaft 900, as illustrated in a graph 912 in FIG. 10C.

To calibrate the shaft 900 at its initialization when it is coupled to a tool driver of a robotic surgical system, once the robotic system recognizes that the tool with the shaft 900 having the conductive feature 902 is installed, the sensor 904 senses the inductance. The sensed inductance values are compared to previously acquired inductance values that are stored in association with respective shaft angle value. The rotation angle of the shaft 900 is determined based on the comparison.

As mentioned above, in the examples discussed in above, voltage values acquired by at least one sensor configured to sense a position of at least one target associated with tool shaft can be calibrated relative to shaft rotation angles during manufacturing and/or assembly of the surgical tool having the shaft. Thus, it can be determined which voltage is to be sensed by the sensor at each rotation angle of the shaft. These calibration values can be stored in a suitable storage, such as in a non-volatile memory, in the surgical tool. For example, as shown in FIG. 12B, the tool can include (e.g., in its housing) a microcontroller including at least one processor and memory. The processor can cause the calibration values to be stored in the memory and it can be used to access the values from the memory when the tool is in use. Additionally or alternatively, the calibration values can be stored in a suitable database accessible by the robotic system. The database can be stored in memory located at a remote computing device with which the robotic system can communicate.

Regardless of the specific location at which the calibration values are stored, these values can be accessed when the shaft is coupled with the tool driver. In this way, a value of voltage sensed by the sensor can be compared to the calibration voltage values to identify a matching voltage value. A value of the shaft angle corresponding to the matching voltage value is identified as the current rotation angle of the shaft.

Figure 11:
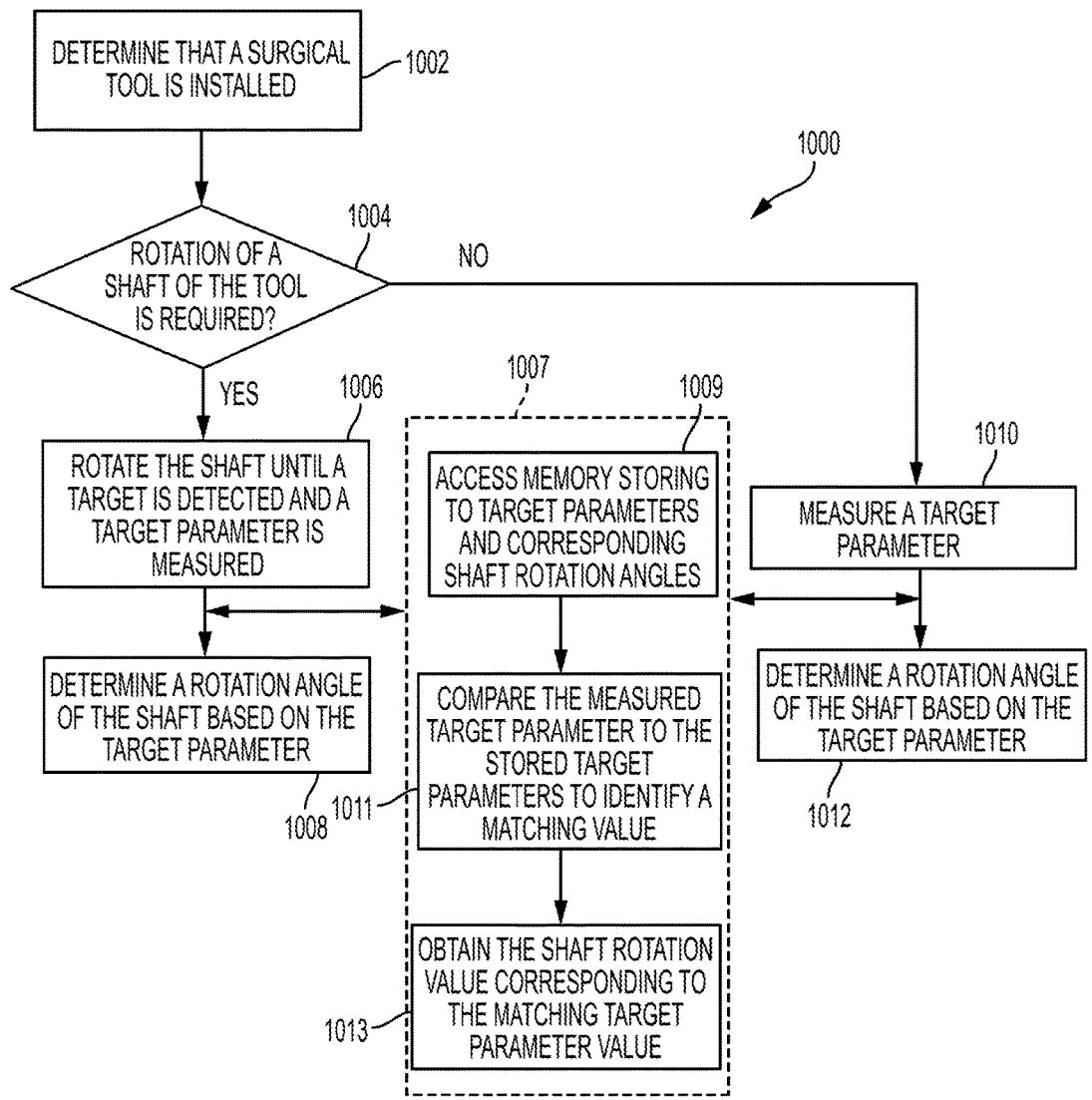
FIG. 11 is a flowchart of a process of calibration of a shaft of a surgical tool in accordance with the described subject matter.

In the embodiments described above, a shaft of a surgical tool can be calibrated when the tool is coupled to a tool driver of an electromechanical arm of a robotic surgical system. The calibration is performed using at least one target associated with the shaft (e.g., coupled to the shaft, formed as one or more portions of the shaft, etc.) and at least one sensor configured to sense the position of the target. FIG. 11 illustrates generally a method or process 1000 of calibration of a rotation angle of the shaft to establish a zero-angle position of the shaft in which its rotation angle with respect to the housing of the tool is set to be zero.

As shown in FIG. 11, at block 1002, it is determined that a surgical tool is installed on the robotic surgical system. At decision block 1004, it is determined whether rotation of the shaft of the tool is required for the calibration. It should be appreciated that this step is shown by way of example only, since it can be optional because the robotic system may know (e.g., from the type of the tool or based on other factors) whether rotation of the shaft of the tool is required. In this example, when the rotation is required, the process 1000 can proceed to block 1006 where the shaft is rotated until a target is detected and a target parameter is measured. This can be done in various ways, for example, using the sensors and corresponding targets as discussed above.

A rotation angle of the shaft is determined based on the target parameter, at block 1008. The rotation angle can be determined at generally shown at block 1007. In particular, a suitable computing system (e.g., system 1100 in FIG. 12A) associated with the robotic surgical system can receive information acquired by the sensors and process this information to determine the rotation angle. For example, as shown at sub-blocks of the block 1007 in FIG. 11, a suitable memory (e.g., memory 1122 in FIG. 12B, discussed below) storing target parameters and corresponding shaft rotation angles can be accessed (block 1009), the measured target parameter can be compared to the stored target parameters to identify a matching value (block 1011), and the shaft rotation value corresponding to the matching target parameter value can be obtained (block 1013). This shaft rotation value can be taken as the rotation angle of the shaft.

Referring back to block 1004, if it is determined that rotation of the shaft of the tool is not required for the calibration, the process 1000 can proceed to block 1010 where a target parameter is measured. This can be done in various ways, for example, using the sensors and corresponding targets as discussed above. A rotation angle of the shaft is then determined based on the target parameter, at block 1012. This can also be done using the processing at block 1007, as discussed above.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 12A:
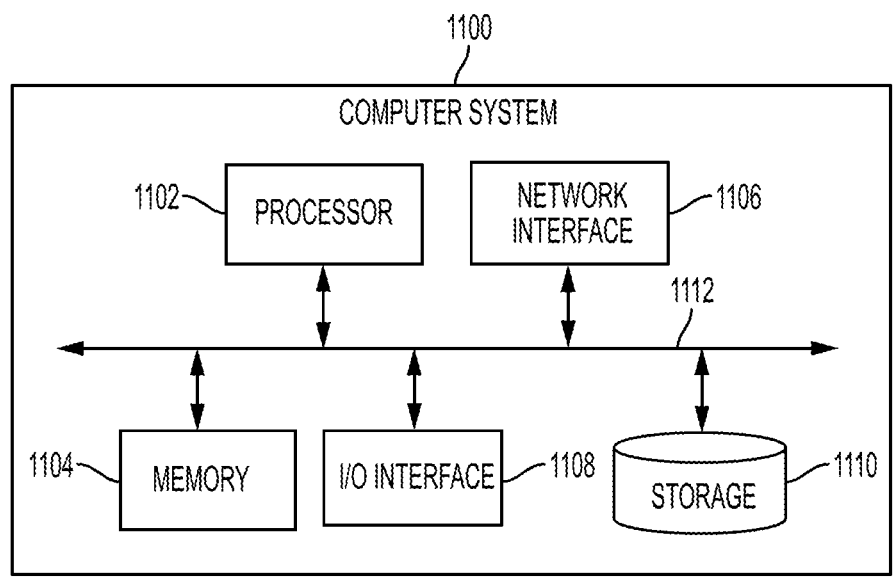
FIG. 12A is a block diagram of one embodiment of a computer system.
Figure 12B:
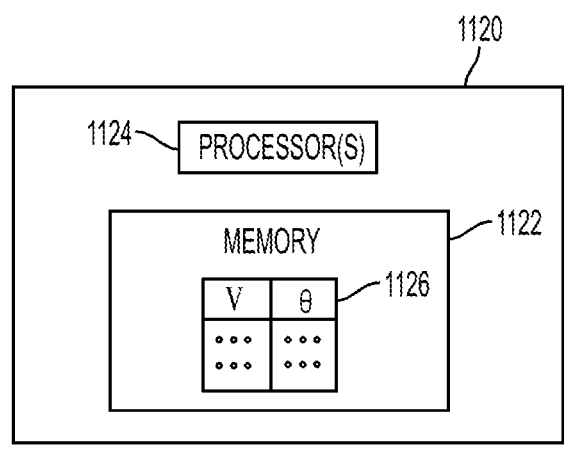
FIG. 12B is a block diagram of one embodiment of a microcontroller.

FIG. 12A illustrates one exemplary embodiment of a computer system 1100. As shown, the computer system 1100 includes one or more processors 1102 which can control the operation of the computer system 1100. "Processors" are also referred to herein as "controllers." The processor(s) 1102 can include any type of microprocessor or central processing unit (CPU), including programmable general-purpose or special-purpose microprocessors and/or any one of a variety of proprietary or commercially available single or multi-processor systems. The computer system 1100 can also include one or more memories 1104, which can provide temporary storage for code to be executed by the processor(s) 1102 or for data acquired from one or more users, storage devices, and/or databases. The memory 1104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1100 can be coupled to a bus system 1112. The illustrated bus system 1112 is an abstraction that represents any one or more separate physical busses, communication lines/interfaces, and/or multi-drop or point-to-point connections, connected by appropriate bridges, adapters, and/or controllers. The computer system 1100 can also include one or more network interface(s) 1106, one or more input/output (TO) interface(s) 1108, and one or more storage device(s) 1110.

The network interface(s) 1106 can enable the computer system 1100 to communicate with remote devices, e.g., other computer systems, over a network, and can be, for non-limiting example, remote desktop connection interfaces, Ethernet adapters, and/or other local area network (LAN) adapters. The IO interface(s) 1108 can include one or more interface components to connect the computer system 1100 with other electronic equipment. For non-limiting example, the IO interface(s) 1108 can include high speed data ports, such as universal serial bus (USB) ports, 1394 ports, Wi-Fi, Bluetooth, etc. Additionally, the computer system 1100 can be accessible to a human user, and thus the IO interface(s) 1108 can include displays, speakers, keyboards, pointing devices, and/or various other video, audio, or alphanumeric interfaces. The storage device(s) 1110 can include any conventional medium for storing data in a non-volatile and/or non-transient manner. The storage device(s) 1110 can thus hold data and/or instructions in a persistent state, i.e., the value(s) are retained despite interruption of power to the computer system 1100. The storage device(s) 1110 can include one or more hard disk drives, flash drives, USB drives, optical drives, various media cards, diskettes, compact discs, and/or any combination thereof and can be directly connected to the computer system 1100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 12A can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

In some embodiments, the computer system 1100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 300 can also include a web server for generating and/or delivering the web pages to client computer systems.

In an exemplary embodiment, the computer system 300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

As discussed above, a surgical tool having a shaft associated with a target such that the target's position can be detected using at least one sensor, can include a controller. The controller can be, for example, a microcontroller. The microcontroller can be configured generally similar to the computer system 1100, though some of the components can be different. For example, the microcontroller can include at least one processor and memory (e.g., memory similar to memory 1104 and/or storage 1110 in FIG. 12A) configured to be accessed by the processor. The memory can store calibration information that can be recorded into the memory during manufacturing of the surgical tool. Additionally or alternatively, this information can be recoded into the memory during use of the surgical tool. The information can include, for example, a plurality of first values representing positions of a target with respect to a sensor, and a plurality of second values representing rotational angles of a shaft each corresponding to respective one of the first values.

FIG. 12B illustrates schematically a microcontroller 1120 that can be included in a surgical tool, such as any of the tools describes therein, or any other suitable tool in which the described subject matter can be implemented. A shown, the microcontroller 1120 includes memory 1122 which can store computer-executable instructions (e.g., firmware) for controlling operation of the surgical tool. The microcontroller 1120 also includes one or more processors 1124 configured to, among other functions, access and process information stored in the memory. The memory 1122 can include one or more memories, and it can include a non-volatile memory 1126 configured to store (e.g., in a form of a look-up table) first values representing positions of a target with respect to a sensor, and a plurality of second values (θ) representing rotational angles of a shaft each corresponding to respective one of the first values. In the example of FIG. 12B, the first values are voltage (V) values, though other values can be acquired by the sensor and recorded in the memory 1126 during assembly of the surgical tool in association with corresponding shaft angles.

During calibration of the surgical tool when the tool is installed on a robotic surgical system, the memory 1126 can be accessed to compare a value acquired by a sensor (e.g., voltage (V)) to the first values stored in the memory 1126, to identify a matching value among the first values. The matching value is used to determine the rotation angle of the shaft. The determined rotation angle is then used by the surgical system to as an initial reference angle for controlling rotation of the tool shaft during a surgical procedure.

It should be appreciated that the microcontroller 1120 can include other components not shown in FIG. 12B for the sake of simplicity. For example, similar to the computer system 1100, the microcontroller 1120 includes an I/O interface that enables it to communicate with suitable components of the surgical system configured to control operation of the surgical tool. In particular, the rotation angle of the shaft determined during the calibration process can be communicated to a controller controlling operation of one or more actuators of the robotic system (e.g., tool driver actuators), such that the actuators control rotation of the shaft of the tool with reference to the determined initial rotation angle (which can be a zero angle).

Furthermore, it should be appreciated that, as mentioned above, the information on the first and second values as stored in the memory 1126 in FIG. 12B, can additionally or alternatively be stored at a suitable location on a robotic surgical system. In some implementations, the information can also be stored in a remote database that is remote to the surgical system.

In some embodiments, at least one sensor associated with a tool's shaft can acquire information from one or more targets to assist in determining a rotation angle of the shaft during the tool initialization. In some embodiments, another approach can be used to ensure consistency and precision in control of the surgical tool, including rotation of a shaft coupled thereto, during a surgical procedure.

Accordingly, in some embodiments, a shaft locking mechanism is used to maintain a desired shaft angle of a shaft of a surgical tool. The shaft may be unintentionally rotated when its rotation is not desired. This can occur, for example, due to user actions, during shipping of the tool, and for various other reasons. However, when such undesirable and/or rotation of the shaft occurs and the tool with the shaft is then coupled to a robotic system, the system may not be able to determine that the rotation happened. Also, the robotic system will not know the degree of the shaft rotation when unintentional rotation takes places. Thus, techniques for preventing rotation of the shaft of the surgical tool when the tool is not coupled to the surgical system are provided.

A rotation angles of the tool shaft relative to a housing of the tool can be determined and recorded (e.g., in a tool's memory or in other storage location(s)) during manufacturing and/or assembly of the surgical tool. The tool shaft is locked at that known rotation angle such that, once the tool is coupled to a robotic surgical system, the robotic system can access the stored value of shaft rotation angle. The shaft is then unlocked and allowed to rotate by the robotic system, e.g., via a tool driver actuator, while the obtained shaft rotation angle can be used a reference value—i.e. it is associated with a known rotation angle of the tool driver actuator of the robotic system. Each time the surgical tool is disconnected from the robotic system, the system records the last rotation angle of the shaft (e.g., in the tool's memory or in the system) and the shaft is locked at that angle. In this way, arbitrary shaft rotation is prevented, while the robotic system is able to determine a shaft rotation angle at each point of operation of the surgical tool.

FIGS. 13A, 13B, 13C, 14A, and 14B illustrate one embodiment of a shaft locking mechanism 1202 configured to prevent rotation of a shaft 1200 of a surgical tool (not shown) configured to be coupled to an electromechanical arm of a robotic surgical system. The shaft locking mechanism 1202 can be disposed on a proximal end of the shaft 1200 and it includes an adapter 1203 circumferentially and non-movably coupled to the proximal end of the shaft 1200, an input gear 1204 also circumferentially coupled to the proximal end of the shaft 1200 proximally of the adapter 1203, and an outer ring 1206 non-movably coupled to the tool in a suitable manner and disposed circumferentially around (without engaging with) the input gear 1204. The shaft locking mechanism 1202 also includes pins 1208a-

1208d that are configured to assist in operation of the mechanism 1202 as described below. The pins 1208a-1208d can be coupled to a suitable component in the tool.

The shaft locking mechanism 1202 is configured to reversibly engage with the electromechanical arm (e.g., a tool driver). In particular, the input gear 1204 is configured to reversibly engage with one or more input actuators on the electromechanical arm, e.g., on a tool driver. For example, referring back to FIG. 3, one of the motors 314a-314d can be configured to reversibly mate with the input gear 1204 when the tool having the input gear 1204 is coupled to the tool driver 308. It should be appreciated, however, that the shaft locking mechanism 1202 can be included in a surgical tool configured to reversibly mate with any suitable tool driver. In addition, although by way of example, the tool driver 308 in FIG. 3 is shown to include least one sensor 342 configured to detect a position of at least one target 340 disposed on a shaft of a surgical tool, it should be appreciated that shaft locking mechanism 1202 can be included in the surgical tool that does not include a target. Likewise, the tool driver that can mate with such tool similarly does not include a sensor for detection of the target. Regardless of the configuration of the tool driver and its component(s) configured to apply torque to the input gear 1204, the shaft locking mechanism 1202 can operate to prevent undesirable shaft rotation.

When the tool is not connected to the tool driver of the robotic surgical system, the input gear 1204 is not coupled to the driver's rotary input actuators and the shaft 1200 is prevented from being rotated, as discussed in more detail below. When the tool is coupled to the tool driver, the input gear 1204 is coupled to the rotary input actuators such that the shaft 1200 can rotate.

The input gear 1204 can have various configurations. In the illustrated embodiments, the input gear 1204 has teeth disposed around its circumference that are configured to engage with the driver's actuators. As shown in FIGS. 13B-14B, the input gear 1204 includes tabs 1210a, 1210b that are configured to be engage the pins 1208a-1208d as discussed below. The tabs 1210a, 1210b are disposed diametrically across from one another with respect to the shaft 1200, as shown in FIGS. 13B-14B.

Figure 13A:
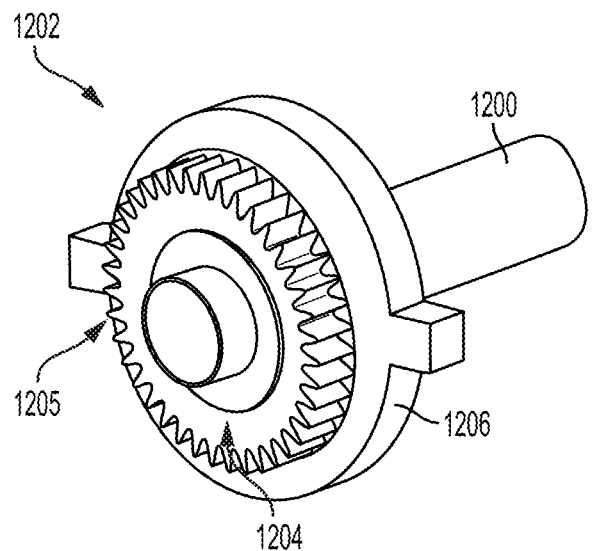
FIG. 13A is a perspective view, from a proximal end, of one embodiment of a proximal portion a shaft of a surgical tool having a shaft locking mechanism.
Figure 13B:
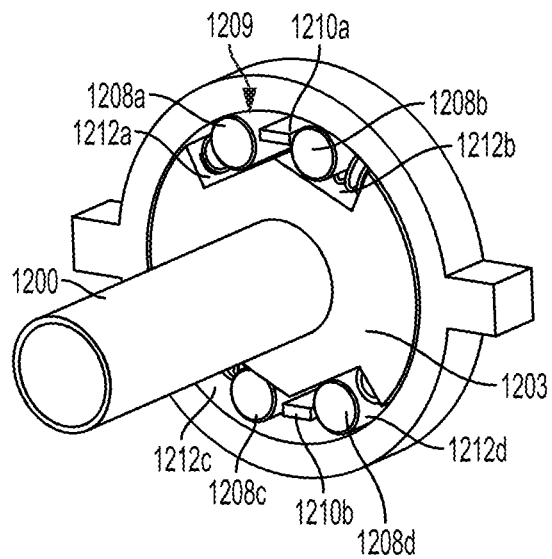
FIG. 13B is a perspective view, from a distal end, of the shaft locking mechanism of FIG. 13A, illustrating a configuration of the shaft locking mechanism in which rotation of the shaft is prevented.

The outer diameter of the input gear 1204 is only slightly smaller than the inner diameter of the outer ring 1206. Thus, as shown in FIGS. 13B and 13C, when the tool (and thus the shaft 1200) is not coupled to the tool driver, ramp surfaces 1212a-1212d formed on the outer surface of the adapter 1203 bias the pins 1208a-1208d into frictional engagement with an inner surface 1209 of the outer ring 1206. As shown in FIGS. 13B-14B, the ramp surfaces 1212a-1212d are formed as cut-outs in the outer surface of the adapter 1203 such that the ramp surfaces 1212a, 1212b are formed on one side of the outer wall of the adapter 1203 and the ramp surfaces 1212c, 1212d are formed on the diametrically opposite side of the adapter's outer wall. The ramp surfaces 1212a, 1212b extend towards each other from inner surfaces of the respective cut-outs that also include adapter pins 1216a, 1216b. Similarly, the ramp surfaces 1212c, 1212d extend towards each other from inner surfaces of the respective cut-outs that also include adapter pins 1216c, 1216d. The adapter pins 1216a-1216d has respective springs 1214a-1214d at least partially disposed thereon. It should be appreciated that the adapter pins 1216a-1216d are shown by way of example only, as the springs 1214a-1214d can be coupled to other elements. Also, in some cases, the adapter pins may not be present.

As shown in FIGS. 13B and 13C, the springs 1214a-1214d bias the pins 1208a-1208d into their positions in which they prevent shaft rotation. In this way, the pins 1208a-1208d positioned between the ramp surfaces 1212a-1212b and the inner surface 1209 prevent rotation of the shaft 1200. Thus, the shaft 1200 is prevented from being rotated when the tool is not coupled to the tool driver.

When the tool is coupled to the tool driver and torque is thus applied to the input gear 1204, the tabs 1210a, 1210b can bias the pins 1208a-1208d which push surfaces on the shaft 1200 to cause shaft rotation, as shown in FIGS. 14A and 14B. The shaft 1200 can thus be rotated clockwise and counterclockwise. In particular, FIG. 14A illustrates that, when torque is applied to the input gear 1204 to cause the shaft 1200 to be rotated to the right left, the tabs 1210a, 1210b on the input gear 1204 engage the pins 1208b, 1208c and cause the pins 1208b, 1208c to move off the ramp surfaces 1212b, 1212c. This causes the pins 1208b, 1208c to compress the springs 1214b, 1214c and push the adapter pins 1216b, 1216c to thus cause the shaft 1200 to rotate. In a similar manner, as shown in FIG. 14B, when torque is applied to the input gear 1204 to cause the shaft 1200 to be rotated to the left, the tabs 1210a, 1210b engage the pins 1208a, 1208d and bias the pins off the ramp surfaces 1212a, 1212d. As a result, the pins 1208a, 1208d compress the springs 1214a, 1214d and push the adapter pins 1216a, 1216d to thus cause the shaft 1200 to rotate.

The input gear 1204 can be controlled by the robotic surgical system during a surgical procedure such that the gear 1204 is rotated out of the position in which rotation of the shaft 1200 is prevented. Additionally, the input gear 1204 can be configured to be manually controlled by a user to move into the position in which rotation of the shaft 1200 is prevented. Regardless of the way in which operation of the input gear 1204 is controlled, if at some point during the surgical procedure it is desired to preclude shaft rotation, the input gear 1204 can be rotated in a position in which the pins 1208a-1208d are biased (by the springs 1214a-1214d) against the ramp surfaces 1212a-1212d and between the ramp surfaces 1212a-1212d and the inner surface 1209 of the outer ring 1206. In such configuration, the rotation of the shaft is prevented.

The rotation of the shaft can be prevented in a similar manner when tool and this the input gear 1204 are disconnected from the surgical system. In this way, no torque is any longer applied to the input gear 1204, and the pins 1208a-1208d are biased into engagement between the ramp surfaces 1212a-1212d and the inner surface 1209 of the outer ring 1206.

In the illustrated embodiment, the shaft 1200 is allowed to rotate when the tool with the shaft 1200 is coupled to a tool driver of a robotic surgical system. As discussed above, a value of the rotation angle of the shaft 1200 can be measured during manufacturing and stored in non-volatile memory of the tool. When the tool is installed on the robotic surgical system, the system can access the tool's non-volatile memory to obtain the stored value of the shaft rotation angle. The position of the shaft 1200 is then locked and the stored value of the shaft rotation angle can be used as a reference or initial value of the shaft.

In use, values of a shaft rotation angle are measured by sensors mounted on system motors (e.g., motors disposed on the tool driver), and used to update the original value of the shaft rotation angle stored in the tool's memory during manufacturing. Thus, during a surgical procedure, a value of the shaft rotation angle is updated in the tool's memory (e.g., memory 1122 in FIG. 12B) as a new value is obtained. And before the surgical tool is detached from the tool driver (or other component of the surgical system), the system stores a value of the latest shaft rotation angle to the tool's memory. The shaft 1200 is then decoupled from the surgical system and locked in the position that corresponds to the latest shaft rotation angle. In this way, when the surgical tool is again coupled with the surgical system, the value of the latest shaft rotation angle stored in the memory of the tool can be obtained by the system and used as the reference shaft rotation angle. This process can be repeated until the end of life of the surgical tool.

Preferably, components of the systems and devices described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
   an elongate shaft configured to be coupled to an electromechanical arm of a robotic surgical system and having an end effector coupled to a distal end thereof, the elongate shaft being rotatable about a longitudinal axis of the elongate shaft; and
   at least one target associated with the elongate shaft and configured to be non-independently movable with respect to the elongate shaft, wherein a position of the target is detected using at least one sensor disposed on the electromechanical arm of the robotic surgical system such that the elongate shaft is able to move independently of the sensor, and wherein the detected position is used to determine a rotational angle of the elongate shaft.

2. The surgical tool of claim 1, wherein the sensor is at a position so as to be remote from the elongate shaft.

3. The surgical tool of claim 1, wherein the at least one target is coupled to the elongate shaft.

4. The surgical tool of claim 1, wherein the at least one target comprises a portion of the elongate shaft having properties distinct from a remainder of the elongate shaft.

5. The surgical tool of claim 1, wherein the at least one target is associated with the elongate shaft such that a position of the target, when detected, is used to determine a zero rotational angle position of the elongate shaft.

6. The tool of claim 1, wherein the target comprises at least one substantially circular magnetic feature disposed in the elongate shaft coaxially therewith, and the at least one sensor comprises first and second sensors.

7. The surgical tool of claim 1, wherein the at least one target comprises at least one portion of the elongate shaft that is magnetized and disposed at least partially along a circumference of the elongate shaft, and the at least one sensor comprises first and second sensors.

8. The surgical tool of claim 1, wherein the at least one target comprises at least one portion of the elongate shaft that is disposed at least partially along a circumference of the elongate shaft, the at least one portion having at least one light absorption property that is different from at least one light absorption property of a remainder of the elongate shaft, and wherein the at least one sensor comprises a transmitter and a receiver.

9. The surgical tool of claim 1, wherein the at least one target comprises an elongate magnetic element having first and second ends and disposed substantially helically around the elongate shaft, and the at least one sensor is disposed adjacent to one of the first and second ends.

10. The surgical tool of claim 1, wherein the at least one target comprises at least one magnet disposed at a predetermined position along the elongate shaft and offset from a central longitudinal axis of the elongate shaft.

11. The surgical tool of claim 1, wherein the at least one target comprises at least one substantially circular conductive feature disposed around a circumference of the elongate shaft, and the at least one sensor comprises an inductive sensor.

12. The surgical tool of claim 1, further comprising:
   a memory configured to store a plurality of first values representing positions of the target with respect to the sensor, and a plurality of second values representing rotational angles of the elongate shaft each corresponding to respective one of the first values.

13. The surgical tool of claim 12, wherein the tool is further configured to receive a user-initiated input requesting rotational movement of the elongate shaft with reference to the stored values.

14. The surgical tool of claim 12, further comprising a controller configured to receive a user-initiated input requesting rotational movement of the elongate shaft with reference to the stored values.

15. A method of operating a surgical tool, comprising:
   detecting a connection between an elongate shaft and an electromechanical arm of a robotic surgical system, the elongate shaft having an end effector coupled to a distal end thereof and being rotatable about a longitudinal axis thereof, and having at least one target associated therewith that is configured to be movable together with the elongate shaft;
   acquiring, by a sensor disposed on the electromechanical arm of the robotic surgical system, at least one value corresponding to a position of the target with respect to the sensor; and
   determining, by a processor in operable communication with the sensor, a rotational angle of the elongate shaft based on the acquired value.

16. The method of claim 15, further comprising:
   receiving a user-initiated input requesting rotational movement of the elongate shaft to position the elongate shaft such that the sensor is able to acquire the at least one value indicating the position of the target with respect to the sensor.

17. The method of claim 15, further comprising:
accessing a storage storing a plurality of first values representing positions of the target with respect to the sensor, and a plurality of second values representing rotational angles of the elongate shaft each corresponding to respective one of the first value;
comparing the acquired value to the plurality of first values to identify a matching first value; and
determining the rotational angle of the elongate shaft based on a second value of the plurality of second values that corresponds to the matching first value.

18. The method of claim 15, wherein the at least one value is a voltage value.

19. A robotic surgical system, comprising:
a surgical tool having
an elongate shaft configured to be coupled to an electromechanical arm of the robotic surgical system and having an end effector coupled to a distal end thereof, the elongate shaft being rotatable about a longitudinal axis thereof; and
at least one target associated with the elongate shaft and configured to be non-independently movable with respect to the elongate shaft;
at least one sensor disposed on the electromechanical arm and configured to detect a position of the target, wherein the detected position is used to determine a rotational angle of the elongate shaft;
a memory configured to store a plurality of first values representing positions of the target with respect to the sensor, and a plurality of second values representing rotational angles of the elongate shaft each corresponding to respective one of the first values; and
a controller configured to access the memory to determine the rotational angle of the elongate shaft based on a comparison of the detected position of the target with the plurality of first values.

* * * * *